United States Patent [19]
Gugel et al.

[11] Patent Number: 4,672,852
[45] Date of Patent: Jun. 16, 1987

[54] TEST MANIPULATOR EXTERNALLY APPLICABLE TO A PIPE

[75] Inventors: Georg Gugel, Kalchreuth; Erich Haas, Leinburg, both of Fed. Rep. of Germany

[73] Assignee: Kraftwerk Union Aktiengesellschaft, Mulheim an der Ruhr, Fed. Rep. of Germany

[21] Appl. No.: 641,572

[22] Filed: Aug. 16, 1984

[30] Foreign Application Priority Data

Aug. 16, 1983 [DE] Fed. Rep. of Germany ....... 3329483

[51] Int. Cl.$^4$ ............................................. G01V 29/04
[52] U.S. Cl. ........................................ 73/622; 73/637; 73/638; 73/640
[58] Field of Search ................. 73/622, 640, 637, 638, 73/635

[56] References Cited
U.S. PATENT DOCUMENTS

| | | | |
|---|---|---|---|
| 4,331,034 | 5/1982 | Takeda et al. | 73/637 |
| 4,383,448 | 5/1983 | Fujimoto et al. | 73/637 |
| 4,387,598 | 6/1983 | Jamieson | 73/622 |
| 4,389,894 | 6/1983 | Kajiyama | 73/637 |
| 4,474,064 | 10/1984 | Naruse et al. | 73/622 |

FOREIGN PATENT DOCUMENTS

| | | | |
|---|---|---|---|
| 0104655 | 4/1984 | European Pat. Off. | 73/635 |
| 2726612 | 12/1978 | Fed. Rep. of Germany | 73/637 |

*Primary Examiner*—Howard A. Birmiel
*Attorney, Agent, or Firm*—Herbert L. Lerner; Laurence A. Greenberg

[57] ABSTRACT

A test manipulator externally applicable to a pipe, preferably for ultrasonically testing welded seams, the manipulator having a divided race for surrounding a pipe which is to be tested, a guide segment guiding the race at the periphery thereof, a test system carrier drivable in peripheral direction around the pipe, a driving and positioning device for the test system carrier and at least one test head holder fastenable to the test system carrier includes clamping means for fastening the race directly to the pipe in centered relationship to an adjustment mark located on the pipe; a guide segment mounted so as to be movable along the periphery of the race; an outrigger unit flangeable, together with the test system carrier and the test head holder, to the guide segment; and a saddle fastenable to the pipe in centered relationship to the adjustment mark; alternatively, during testing of a so-called pipe connection seam, the guide segment being movable on the saddle in axial direction of the pipe, and the race, together with the test system carrier being rotatable on the guide segment in peripheral direction around the pipe.

12 Claims, 15 Drawing Figures

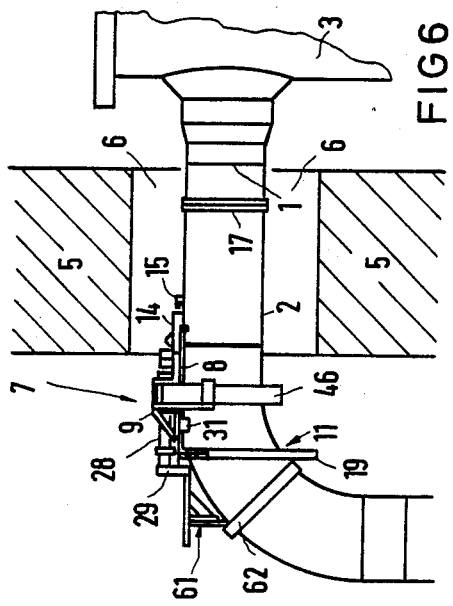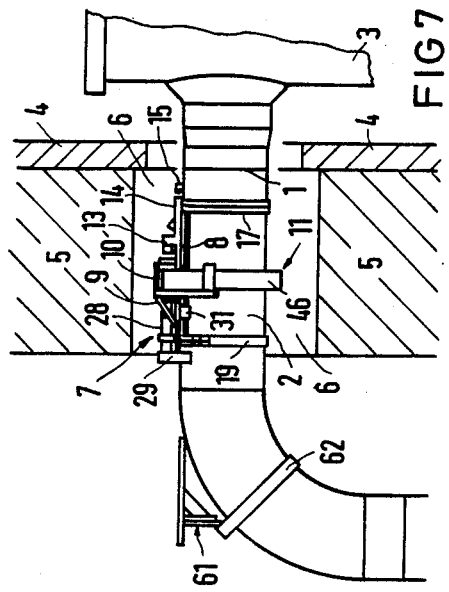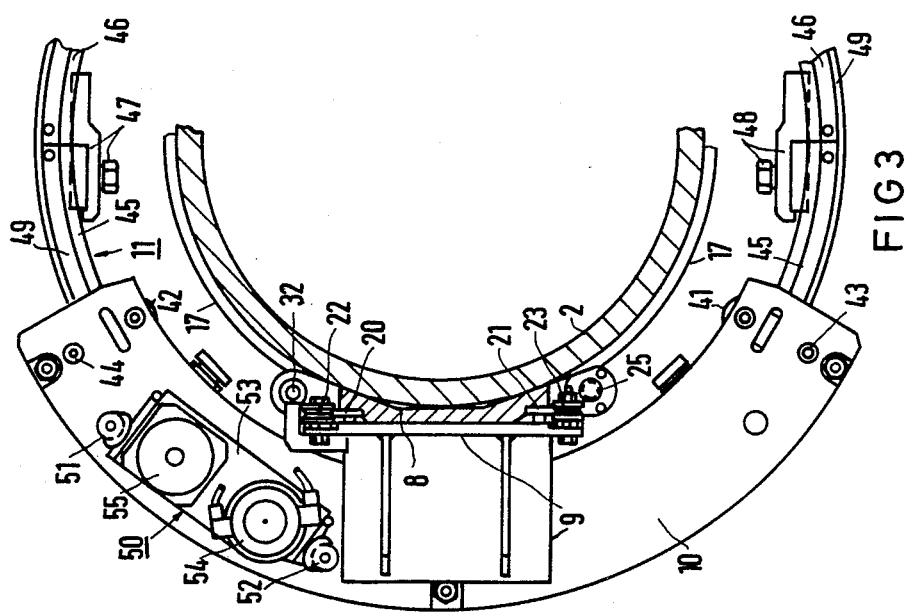

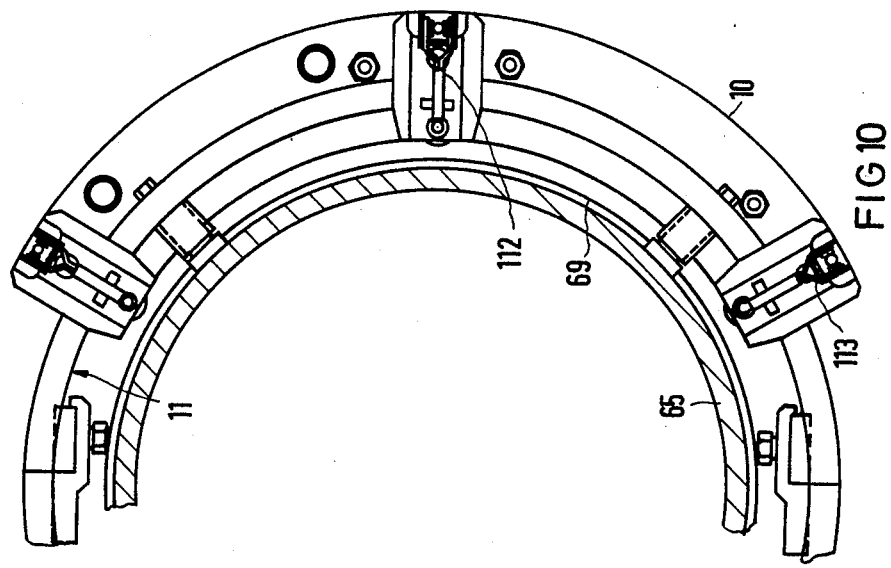
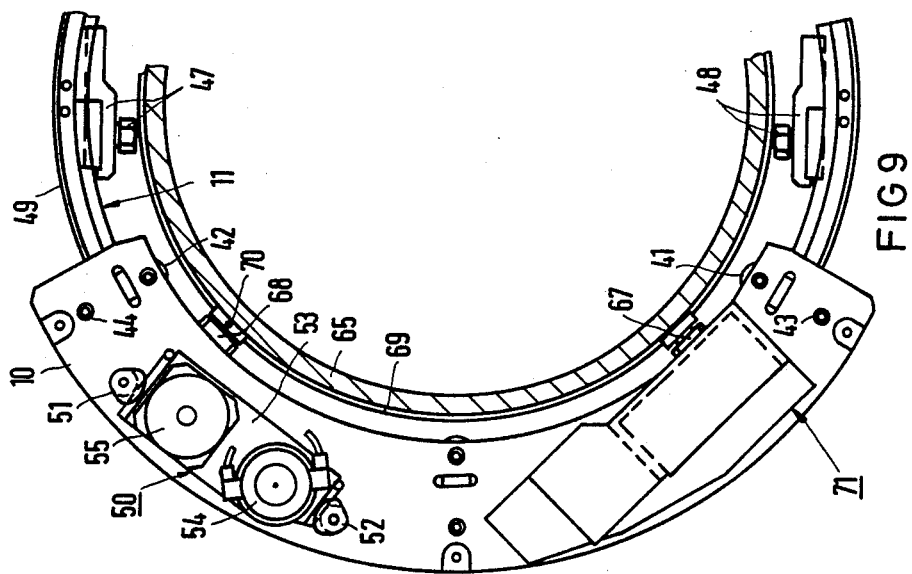

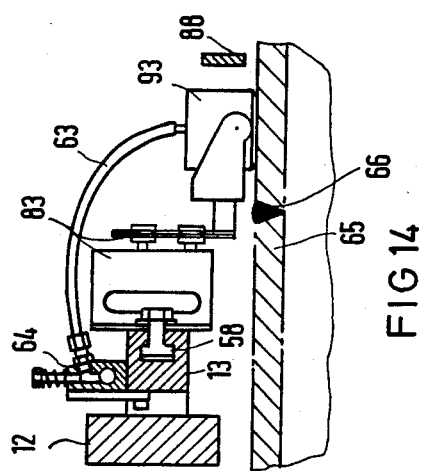
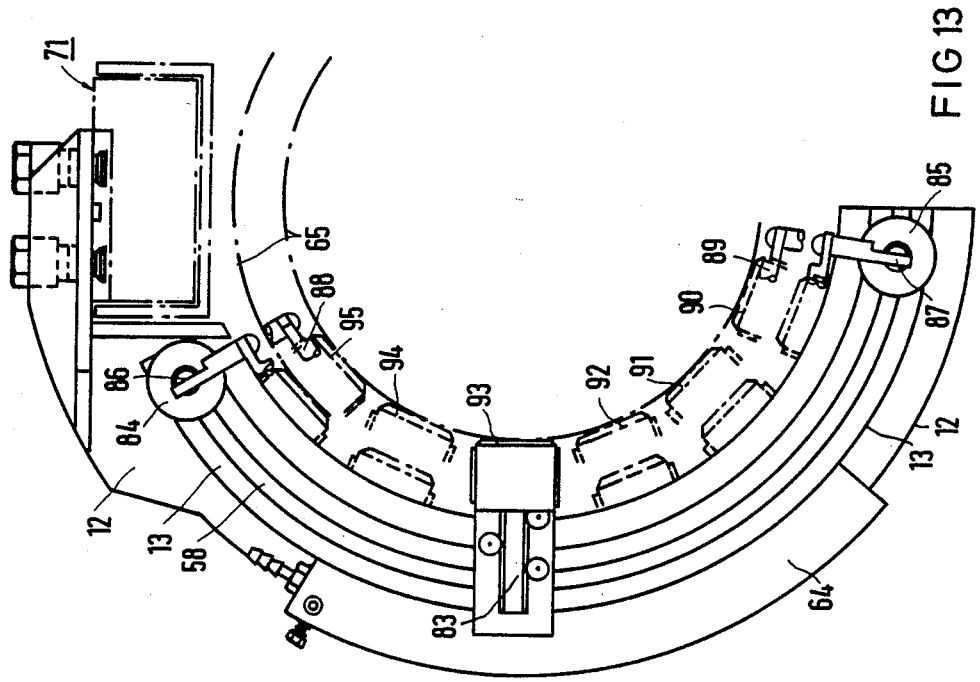

TEST MANIPULATOR EXTERNALLY APPLICABLE TO A PIPE

The invention relates to a test manipulator externally applicable to a pipe, and, more particularly, to such a test manipulator which is preferably for ultrasonically testing welded seams, and which has a divided race for surrounding a pipe which is to be tested, a guide segment for guiding the race at the periphery thereof, a test system carrier drivable in peripheral direction around the pipe, a driving and positioning device for the test system carrier, and at least one test head holder fastenable to the testing system carrier.

A test manipulator which is applicable to the outside of the coolant line of a reactor pressure vessel, by which the welded seam with which the coolant line is welded to the reactor pressure vessel can be tested, has become known heretofore from German Published Non-Prosecuted Application (DE-OS) No. 27 26 612. In this test manipulator, which takes into consideration the confined spatial conditions in vicinity of the line penetration or opening in the biological shield, a so-called saddle is clamped to the coolant line to be tested. On this saddle, a slide or carriage is mounted so as to be movable parallel to the longitudinal axis of the pipe. The slide is a carrier of a test head holder. The latter is fastened to an annular frame mounted so as to be rotatable in peripheral direction. With this construction it is possible to drive into the narrow annular gap between the coolant pipe and the biological shield, and to test the connecting seam of the coolant line at the reactor pressure vessel. It is a peculiarity of this test manipulator that it is less suitable for testing in the region of short, straight pipe sections or at thermally insulated pipes precisely because of properties which predestine it for the testing of pipe connection seams.

It is an object of the invention to provide such a test manipulator wherein the cost of checking welded seams in pipelines is reduced. In particular, it is an object of the invention to provide a test manipulator with which, as much as possible, all welded seams found at the pipes of a power generating station can be checked equally well. The space requirements for applying or mounting the test manipulator on a pipe line should be as little as possible, so that, for example, excessively large parts of thermal insulation need not be removed in the case of pipelines which are thermally insulated.

It is a further object of the invention to provide such a test manipulator which may be installed at the object to be tested in as simple a manner as possible. Finally, it is an object to provide such a test manipulator which would deliver qualitatively and quantitatively exactly comparable measuring results during repeated in-service testing, so that changes, which may have taken place in the interim, can be determined quickly and simply.

With the foregoing and other objects in view, there is provided, in accordance with the invention, a test manipulator externally applicable to a pipe, preferably for ultrasonically testing welded seams, the manipulator having a divided race for surrounding a pipe which is to be tested, a guide segment guiding the race at the periphery thereof, a test system carrier drivable in peripheral direction around the pipe, a driving and positioning device for the test system carrier and at least one test head holder fastenable to the test system carrier, comprising clamping means for fastening the race directly to the pipe in centered relationship to an adjustment mark located on the pipe; a guide segment mounted so as to be movable along the periphery of the race; an outrigger unit flangeable, together with the test system carrier and the test head holder, to the guide segment; and a saddle fastenable to the pipe in centered relationship to the adjustment mark; alternatively, during testing of a so-called pipe connection seam, the guide segment being movable on said saddle in axial direction of the pipe, and the race, together with the test system carrier being rotatable on the guide segment in peripheral direction around the pipe.

With this varying relationship of the individual components of the testing manipulator, the latter can be employed equally well on short sections of the pipe string, from which thermal insulation surrounding the pipe was previously removed, as well as for testing so-called pipe connection seams. The latter are welded seams which connect a pipe to a vessel. Thus, for example, in a reactor pressure vessel, wherein the coolant pipes are passed through thermal insulation and a biological shield, an annular gap exists which extends relatively deeply in axial direction and which, in axial direction has extremely cramped space.

The field of application of the testing manipulator can further be expanded considerably when, in accordance with the invention, the test manipulator has a plurality of the races, the guide segments and the test system carriers of varying size for matching pipes to be tested which are of varying diameters, the driving and positioning device, the saddle and the outrigger unit being, in turn, matched in size thereto. Thereby, the welded seams of practically all of the pipes of a power generating plant can be checked, regardless of the pipe diameters.

In accordance with an additional feature of the invention, there is provided a plurality of the outrigger units, respectively, having strokes of varying length, the outrigger units being flangeable to all of the test system carriers.

In accordance with another feature of the invention, there are provided fast-acting closures for connecting a plurality of the foregoing structural elements to one another.

In accordance with a further feature of the invention, the test head holder is movable parallel to the axis of the pipe on the outrigger unit fastened to the guide segment.

In accordance with still another feature of the invention, the outrigger unit carries a spindle extending parallel to the axis of the pipe, and a spindle unit mounted on the spindle for adjustably displacing the test head holder.

In accordance with still a further feature of the invention, there is provided a geared motor coupled to a pulse transmitter and operatively connected with the spindle unit for adjusting the unit.

In accordance with still an additional feature of the invention, the race is formed with a ring gear, and including a pinion carried by the guide segment and meshing with the ring gear for adjusting the guide segment relative to the race.

In accordance with again another feature of the invention, there is provided a geared motor and a pulse transmitter therefor clampable together on the guide segment, the pinion being drivable by the geared motor.

In accordance with again a further feature of the invention, the adjusting mark is an adjustment pin carried by an adjustment ring clampable around the pipe to be tested.

In accordance with again an additional feature of the invention, there are provided cup springs for prestressing the adjustment ring to absorb thermal expansion.

In accordance with a concomittant feature of the invention, there is provided an auxiliary bracket clampable on a pipe section and downwardly bent pipe elbow, respectively, for assembling the respective structural elements.

Other features which are considered as characteristic for the invention are set forth in the appended claims.

Although the invention is illustrated and described herein as embodied in a test manipulator externally applicable to a pipe, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 3 is a fragmentary cross-sectional view of FIG. 2 taken along the line III—III in direction of the arrows;

FIG. 6 is a view like that of FIG. 5 showing the test manipulator assembled extensively on the pipe;

FIG. 7 is a view like that of FIG. 6 showing the test manipulator in a different location in a final operating position thereof and also showing the saddle fixed on the pipe;

FIG. 9 is a fragmentary cross-sectional view of FIG. 8 taken along the line IX—IX in direction of the arrows;

FIG. 10 is a fragmentary, cross-sectional view of FIG. 8, taken along the line X—X;

FIG. 13 is an elevational view of the test system carrier as viewed from the right hand side of FIG. 12;

FIG. 14 is a cross-sectional view of FIG. 12 taken along the line XIV—XIV in direction of the arrows.

Figure 1:
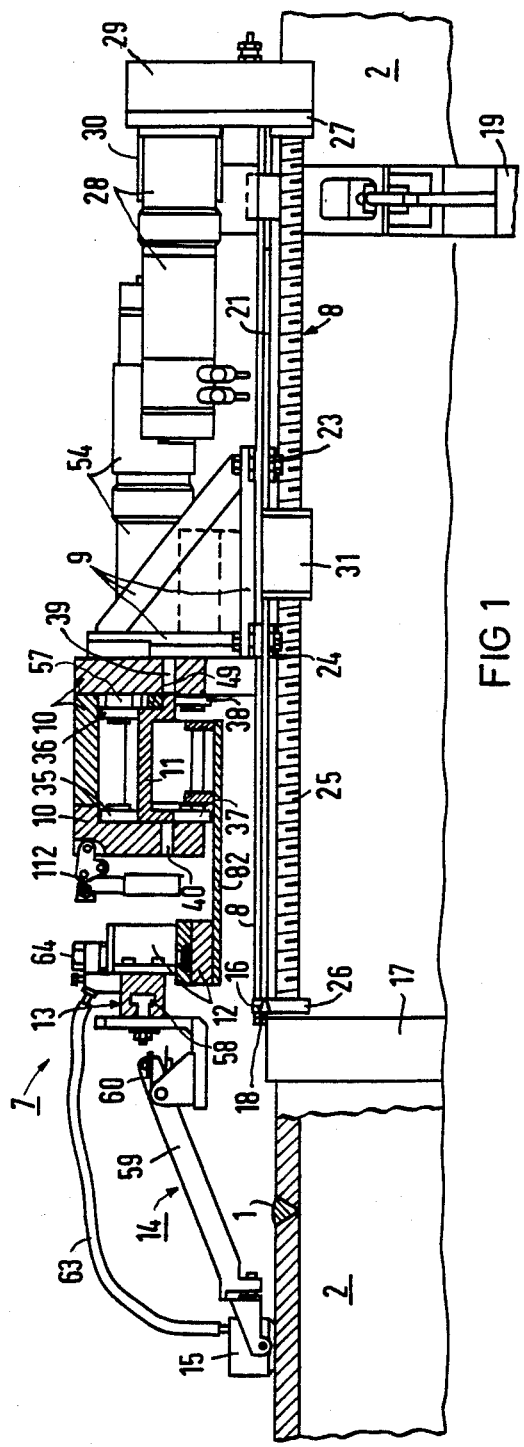
FIG. 1 is a side elevational view, partly in section, of a test manipulator, according to the invention, mounted on a pipe nozzle or joint in operating position during testing of a welded seam.
Figure 4:
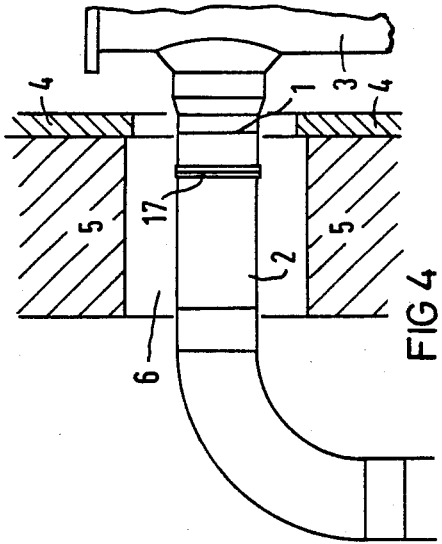
FIG. 4 is a side elevational view, partly in section, of a pipe terminating in a reactor pressure vessel and provided with a pipe-connecting seam to be tested with the test manipulator of FIGS. 1 to 3.

Referring now to the drawing and first, particularly, to FIG. 4 thereof, it is readily apparent that the accessibility of pipe connecting seams 1, especially connecting seams of coolant pipes 2 at a reactor pressure vessel 3, is greatly limited by the required thermal shield 4 as well as by the required biological shield 5. The pipe connecting seam 1 can be reached only via a narrow annular gap 6 between the coolant pipe 2 and the biological and thermal shield. Under these and similar test conditions, the test manipulator 7, as shown in FIG. 1, is made up of a saddle 8 which can be placed on the pipe 2 to be tested; a slide or carriage 9 which can be moved along the saddle; a guide segment 10 which can be fastened to the slide 9; a race 11 mounted in the guide segment so as to be rotatable in peripheral direction thereof; a test system carrier 12 mounted on the race 11; a ledge 13 carried by the test system carrier 12, as well as test head holders 14 (only one of which is shown) fastened to the ledge 13. Each test head holder 14 carries a test head 15 suspended in gimbals.

Figure 2:
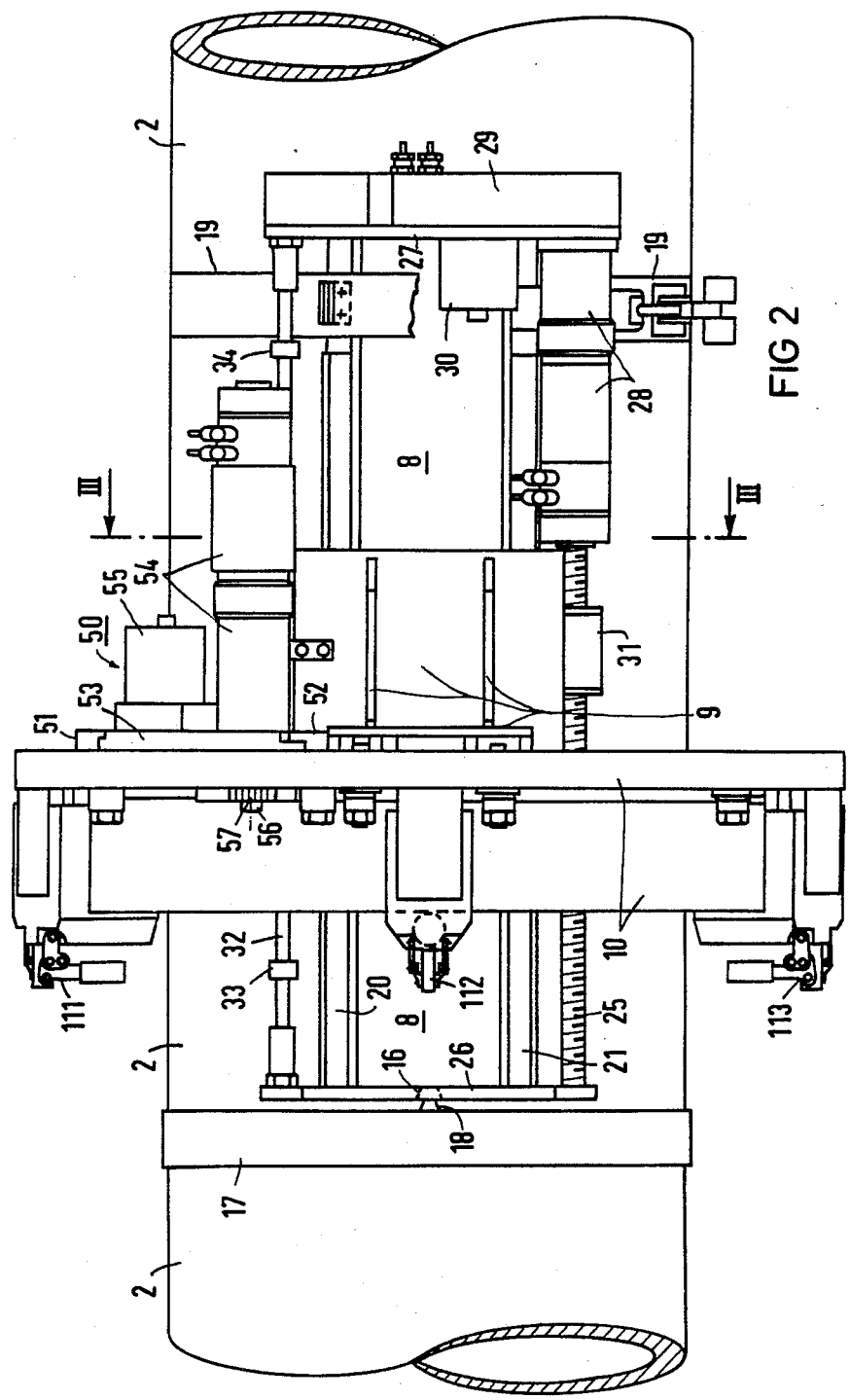
FIG. 2 is a top plan view of FIG. 1 with the test system carrier omitted.

FIGS. 1 and 3 illustrate how the saddle 8 rests directly on the pipe 2 to be tested. On the side thereof facing towards the test heads 15, the saddle 8 is formed with a centering hole 16 which is able to be brought into engagement with an adjustment pin 18 attached to an adjusting ring 17 which is firmly mounted on the pipe. At the other end thereof, the saddle 8 can be clamped tight via a tensioning band 19 which can be placed around the pipe. As FIGS. 2 and 3 show, the saddle 8 carries, on both of the elongated sides thereof, a prismatic or prism-shaped track 20, 21, along which the slide 9 can be driven in longitudinal direction of the saddle via four rollers 22, 23, 24 (only three of which are shown). Parallel and adjacent to the one track 21 is a spindle 25 which is rotatably supported at both end plates 26, 27 of the saddle 8. The spindle 25 is drivable by a geared motor 28 which is flanged to an end plate 27 of the saddle 8. A pulse generator 30 is coupled to a transmission or gearing 29 of the saddle 8. The spindle 25 carries a spindle nut 31 coupled to the slide 9. Parallel and adjacent to the other track 20, as shown in FIG. 2, a control rod 32 is arranged supported so as to be axially displaceable at both end plates 26, 27 of the saddle 8. Two stops 33 and 34 which can be brought into engagement with the slide are clamped to the control rod 32.

As is further illustrated in FIGS. 1 and 2, the guide segment 10 is flanged to the slide 9. This guide segment has a U-shaped cross section. It is curved in a quadrant around the pipe 2 to be tested. In the interior of the guide segment 10, ball bearings 35, 36, 37, 38, 39, 40, 41, 42, 43, 44 are arranged, between which the race 11 is supported so that it can be slid therethrough in peripheral or circumferential direction. As shown in FIG. 3, this race 11 is formed of two semicircular parts 45 and 46 which can be connected to each other by means of two fast-acting clamps 47 and 48. The radius of the race 11 is somewhat larger than the outside radius of the largest pipe to be tested. As will further be shown with the aid of FIG. 15, each race 11 is associated with a specific guide segment 10 matched to its radius. The cross-section of the race 11 is U-shaped. On one side thereof it carries a circular ring gear or rim gear 49. A driving plate 50 is couplable to the guide segment 10 via two clamps 51 and 52. The driving plate 50 is formed of a plate 53, on which a geared motor 54, together with a pulse generator 55, is firmly mounted. On a drive shaft 56 of the geared motor 54, there is mounted a pinion 57 which meshes with the ring gear or gear rim 49 of the race 11.

As shown in FIG. 1, a test system carrier 12 is assembled with the race 11. To the test system carrier 12, there is fastened a so-called ledge 13. This ledge 13, which extends parallel to the race 11 and, like the latter, is curved about the axis of symmetry of the pipe 2, is formed with a fastening slot 58, to which the test head holders 14 (only one of which is shown in FIG. 1) with the test heads 15 thereof are fastenable. Each of the test head holders 14 is formed of a spring-loaded swivel arm 59, to which the test head 15 proper is linked in gimbals. The spring 60 of the swivel arm 59 forces the test head 15 against the object to be tested.

If the pipe-connecting seam 1 between a coolant pipe 2 and a reactor pressure vessel 3, for example, is to be tested with the testing manipulator 7, it is advisable, for reasons of exact reproducibility of the measurement results, to firmly mount a so-called adjusting ring 17 on the pipe to be tested, in the vicinity of the welded seam 1 which is to be tested. This adjusting ring can be clamped around the pipe as a flat band so that, after the testing operation is completed, it can remain under the thermal insulation when the latter is replaced thereafter. The adjusting ring 17 merely serves as a carrier of an immovable marker, namely, an adjusting pin 18 in the embodiment example of FIGS. 1 and 2, which can be brought into centered engagement in a centering hole 16 at the one head or end plate 26 of the saddle 8. By placing the saddle on the pipe to be tested and bringing the centering borehole 16 into engagement in the centering pin 18 of the adjusting ring 17, an always reproducible positioning of the saddle 8 of the test manipulator 7 relative to the welded seam 1 is assured. This provides the prerequisite for comparing the measurement results of different measurements exactly with one another.

Figure 5:
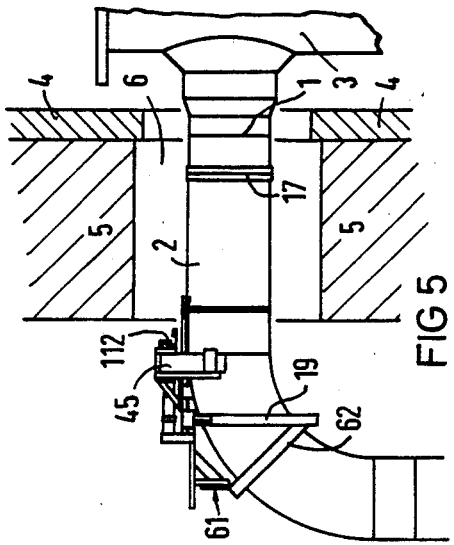
FIG. 5 is a view similar to that of FIG. 4, showing the test manipulator assembled in part on the pipe.

In cases wherein the coolant pipe 2, as shown in the embodiment of FIGS. 4, 5 and 6, changes into a downwardly-directed elbow directly after leaving the reactor pressure vessel, the installation of the test manipulator can be facilitated by first attaching an auxiliary bracket 61 (FIG. 5). The auxiliary bracket 61 can be fastened to the elbow via a tensioning or clamping band 62. It is merely a type of rectilinear extension or elongation of the surface of the pipe section to be tested. The saddle 8 with the slide 9 is placed upon this auxiliary bracket 61 for assembling the test manipulator. The guide segment 10 has already been flanged to the slide 9. A one-half section 45 of the circular race 11 is inserted into the guide segment. The test system carrier 12 has been fastened beforehand to this half race section 45. Then, the drive plate 50 with the geared motor 54 and the pulse generator 55 can be clamped to the guide segment. In this regard, the pinion 5 thereof comes into engagement with the ring gear or gear rim 49 of the inserted half race section 45 and locks the latter. The ledge 13 with the test head holders 14 and the test heads 15 can then be assembled on the test system carrier 12. Finally, the test heads are connected via hoses 63 (only one of which is shown) to a water distributor 64 fastened to the test system carrier 12.

If the saddle 8 is advanced so far that the race 11 is located above the rectilinear pipe section, the other half-section 46 of the race 11 can be coupled by the fast-acting clamping locks 47 and 48 to the first race half-section 45 which is already located in the guide segment. The thus preassembled test manipulator 7 can then be inserted from the auxiliary bracket 61 into the annular gap 6 between the biological and the thermal shielding 4, 5 and the coolant pipe 2. It is advanced so far until the front end plate 26 of the saddle 8 with the centering hole 16 thereof has come into engagement with the adjusting pin 18 of the adjusting ring 17. In this position of the saddle 8, the other end of the saddle is locked to the pipe by the tensioning or clamping band 19. The test manipulator 7 is then ready for testing.

The geared motor 28 of the saddle 8 can be switched from a non-illustrated, radiation-protected control console.

By the action of the geared motor 28, the slider 9 with the guide segment 10, the race 11, the test head system carrier 12 and the test head holders 14, is driven into the annular gap 6 in axial direction via the spindle 25. The respective axial position of the test heads 15 is controllable and reproducible at the control console via the pulse generator 30 coupled to the gearing or transmission 29.

The respective position of the test heads in peripheral direction is variable by switching-on the geared motor 54 flanged to the guide segment 10. It is reproducible exactly via the pulse generator 55 which is fastened to the drive plate 50 and coupled to the geared motor 54. Thus, for in-service tests, the test heads 15 can always be brought into exactly the same measuring position again. The two stops 33 and 34 which are clamped to the control rod 32, serve only to ensure the timely shut-off of the geared motor 54 when the slide 9 approaches the end plates 26 and 27 of the saddle 8.

If a welded seam 66, located in the pipeline 65, is to be checked with the test manipulator 7, it is desirable, because of the heat insulation which encloses the pipe string in many cases, that the test manipulator require as little space as possible in axial direction, so that only a section of the thermal insulation or the heat-retarding material which is as short as possible needs to be removed. To this end, the one half-section 45 of the race 11, which is formed of the two sections 45 and 46, is clamped tightly by means of clamping shoes 67 and 68 to the pipe string 65 to be examined, and preferably to the adjustment ring 69. The one clamping shoe 68 is constructed, in this regard, so that it can be clamped to the adjusting ring 69 only in a defined position relative to the adjusting pin 70 of the adjusting ring. The guide segment 10 can then be slipped on to the half-section 45 of the race 11 fastened to the pipe 65. Thereafter, the second half 46 of the race 11 can be fastened to the first race half-section 45 by means of the fast-action closures 47 and 48, and likewise clamped to the adjustment ring 17 via the non-illustrated clamping shoes.

The driving plate 50 with the drive motor 54 and the pulse generator 55 is flanged again to the guide segment 10 in such a manner that the pinion 57 meshes with the ring gear or gear rim 49 of the race 11.

Figure 8:
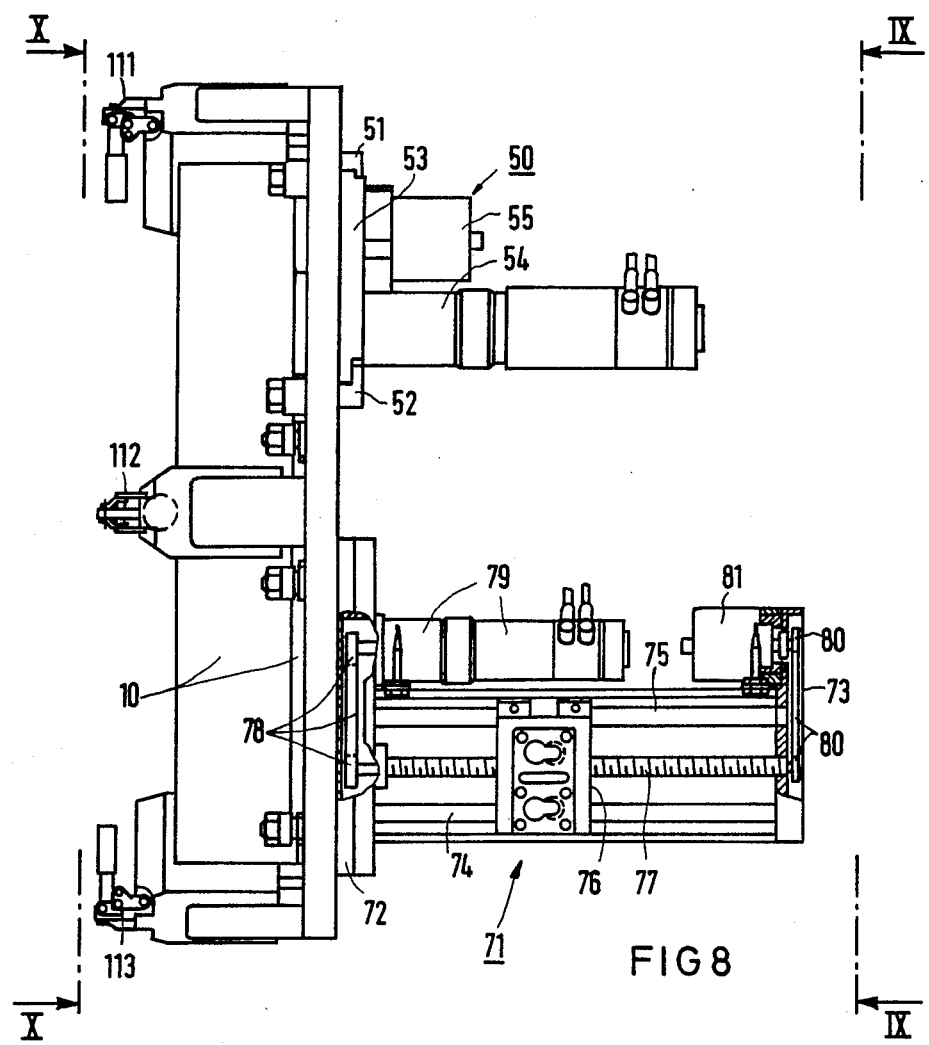
FIG. 8 is a top plan view of the test manipulator with a combination of the components thereof as is used for testing a welded seam located in line with a pipe string.
Figure 11:
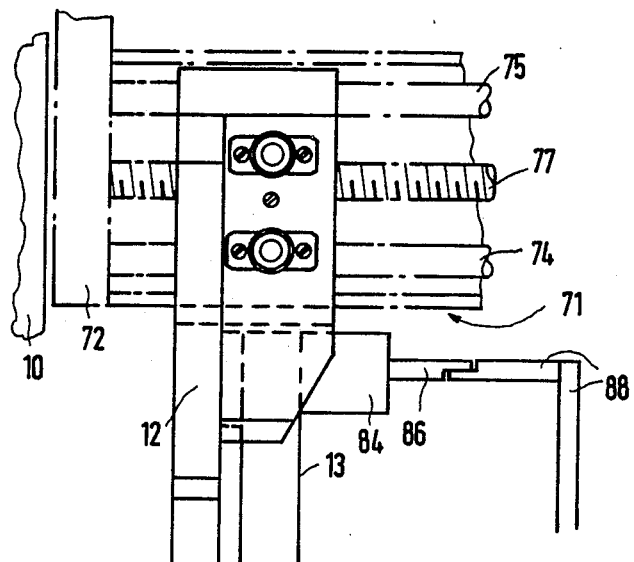
FIG. 11 is a top plan view of the test system carrier mounted on the slide table of FIG. 8.

Instead of the slide 9, an outrigger unit 71 is flanged to the guide segment 10. As shown in FIG. 8, this outrigger unit is formed of two mutually parallel end plates 72 and 73 which are connected to one another via two guide rods 74 and 75 which are parallel to the pipe axis. A slide table 76 is supported for movement along these guide rods. The outrigger unit 71 carries a spindle 77 aligned parallel to the two guide rods 74 and 75. The spindle nut (not visible in FIG. 8) is coupled to the slide table 76. The spindle is coupled via a serrated-belt drive 78 to a geared motor 79 fastened to the one end plate 72. At the other end of the spindle 77, the latter is connected via another serrated-belt drive 80 to a pulse generator 81.

Figure 12:
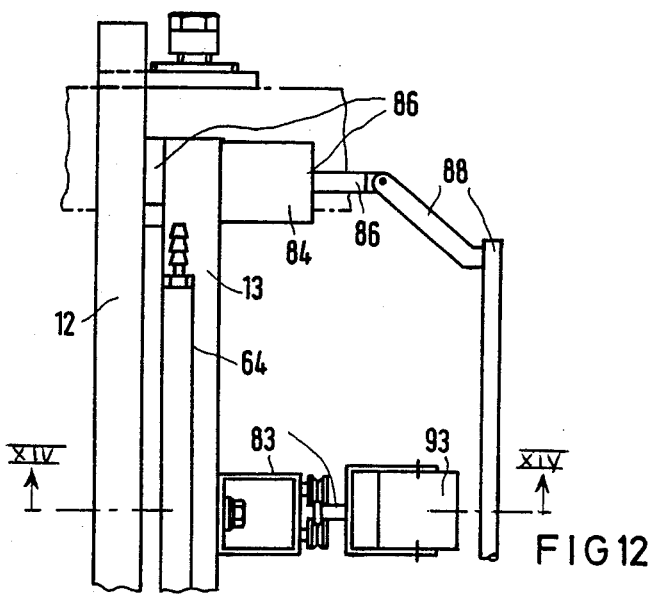
FIG. 12 is a view of the test system carrier as seen from the bottom of FIG. 11, i.e. rotated 90° about the pipe axis.

The test system carrier 12 can be bolted to the slide table 76 shown in FIG. 8. Beforehand, the carrier plate 82 thereof, which is not needed thereat, can be unscrewed. The equipment of the test system carrier 12 is shown in detail in FIGS. 11 to 14. Similarly to the guide segment 10, the test system carrier is curved substantially a quarter circle around the outer periphery of the largest possible pipe to be tested therewith. It supports the ledge 13 which is identical with the ledge of FIGS. 1 and 2. To this ledge 13, there are fastened the test head holders 83 (only one of which is shown) which are described in detail with regard to FIG. 14. In addition, two switches 84 and 85 are fastened to the test system carrier. On the positioning members 86 and 87 thereof, there is mounted a respective shut-off frame 88, 89. The shut-off frames are curved, as shown in FIGS. 12 and 14 in parallel or equidistant relationship to the guide segment 10 around the outer periphery of the pipe 65 to be tested. They are arranged ahead of the test heads 90, 91, 92, 93, 94 and 95 resting against the pipe on the side thereof facing away from the guide segment 10.

In FIGS. 12 and 14, there are seen not only the guidance of the shut-off frames 88 and 89 in front of the test heads, but also the gimbal support thereof in short test head holders 83 screwed tightly in the fastening slot 58 of the ledge 13. Also in this case, a water distributor 63 is mounted on the test system carrier 12. From the water distributor 63, water hoses (only one of which is shown) lead to the individual test heads. Further water suction lines, not illustrated in FIGS. 12 and 14 in the in the interest of clarity, lead from the individual test heads to other connections of the water distributor 63.

If a welded seam 66 located in the pipe string 65 is to be tested, the position of the guide segment 10 is defined in axial direction due to the fastening of the race 11 at the adjustment ring 17. In this regard, however, the axial starting position of the test heads 90 to 95 is only dependent upon the feed of the slide table 76. The latter, however, is exactly reproducible at any time via the pulse generator 81 of the outrigger unit 71 and can be indicated at the remote control console. Also, the position of the race 11 is defined in peripheral direction by centering a given clamping shoe 68 at the adjustment pin of the adjustment ring 69. In conjunction with an otherwise nonillustrated marker, which can be coordinated with the guide segment 10 when it is displaced in peripheral direction, the starting position of the guide segment is also defined in peripheral direction of the race. A given position of the guide segment 10 and, thereby, of the test heads 90 and 95 in peripheral direction can then be reproduced at any time via the pulse generator 55 of the driving plate 50. A prerequisite therefor, however, is the fastening of the test head holders 83 always at the same location of the ledge 13.

When the test manipulator 7 is set into operation, the test heads 90 and 95, starting from the starting position defined at the outset herein, can therefore, be guided around the pipe 65 in peripheral direction by switching-on the geared motor 54 fastened to the driving plate 50 via the pinion 57 which rolls on the ring gear or gear rim 49 of the race 11 and entrains the guide segment 10 in the process. The position which is, in fact, just reached, can be read by means of the number of pulses transmitted by the pulse generator 55 of the driving plate 50 at the remote control console. Similarly, the test heads 90 and 95 can be displaced from the starting position in axial direction by switching on the geared motor 79 flanged to the outrigger unit 71. In the process, the geared motor turns the spindle 77 and, accordingly, displaces the slide table 76 via the spindle nut. The respective position of the test heads in axial direction can then be displayed at the remotely installed control console via the pulse generator 81 driven by the spindle 77. In this manner, every testhead signal can be assigned to a definite geometric location on the pipe 65 and can be compared with the corresponding test signal of a previous measurement. It is a particular advantage of this combination of the test manipulator 7 which is explained in connection with FIGS. 8 to 14 that, in the case of a thermally insulated pipe, the thermal insulation needs to be removed only in a region which corresponds for the most part with the axial displacement of the test heads required for checking the welded seam i.e. corresponds to the length of the outrigger unit 71 plus the width of the guide segment 10 in the axial direction.

Figure 15:
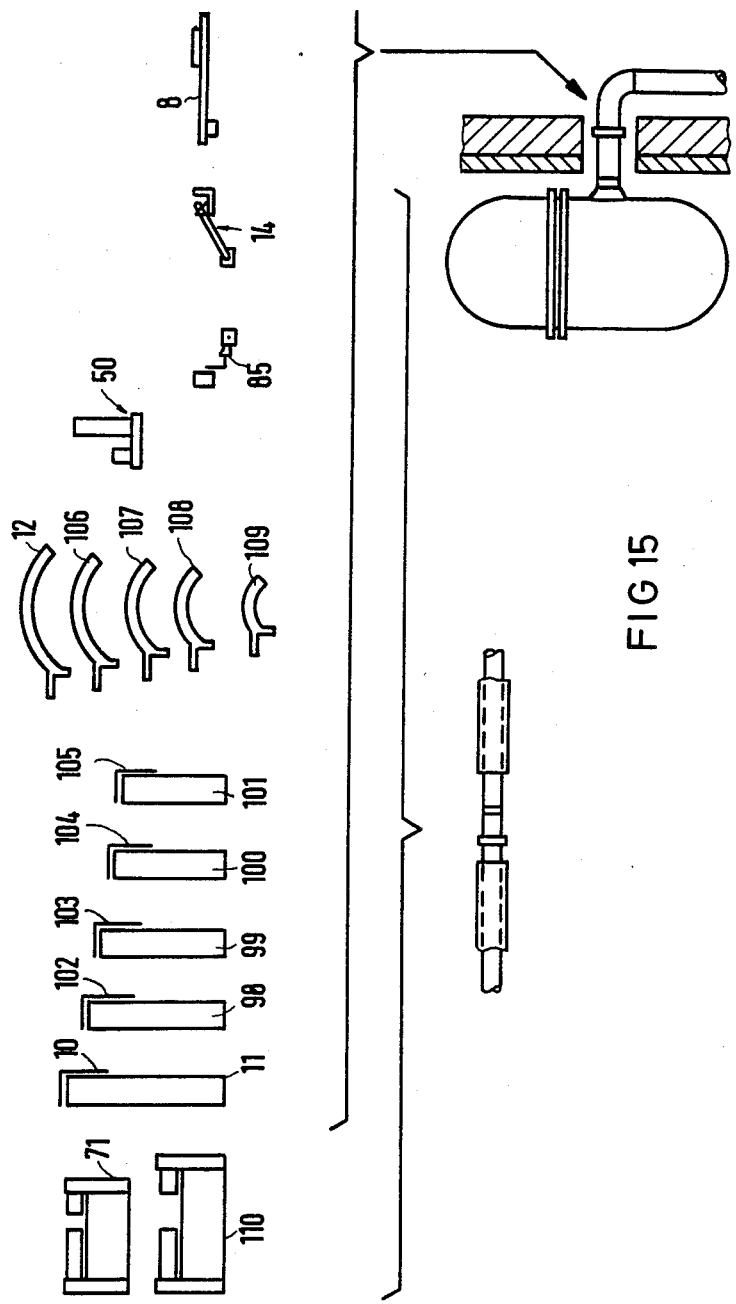
FIG. 15 is an assortment of components of the test manipulator for testing welded seams provided in a pipeline as well as pipe-connecting seams of varying diameters.

FIG. 15 shows in a diagrammatic overview the individual components of the test manipulator 7 which must be combined together for solving the underlying test problem. Thus, the races 11, 98, 99, 100, 101, the guide segments 10, 102, 103, 104, 105 and the test system carriers 12, 106, 107, 108, 109 are constructed for varying pipe-diameter ranges. The test system carriers of a respective pipe-diameter range fit the guide segments, and the latter, in turn, the races of the same diameter range. Several outrigger units, namely two outrigger units 71, 110 in the illustrated embodiment, with strokes of different length, are provided for examining pipes of different thickness. The outrigger unit and the driving plate 50 fit all test system carriers. For testing pipe connecting means, a saddle 8 with an associated slide 9 are provided, the latter being likewise couplable to all test system carriers. Only for pipes having diameters which deviate greatly, could a further saddle (not shown) be provided. The testhead holders 14, 83 shown in FIGS. 1 and 14 fit the ledges 13 (shown only for one pipe diameter) of the associated test system carriers 12, 106, 107, 108, 109. They are interchangeable with one another.

In a testing exercise which is to be performed, the race 11, 98 to 101 of the corresponding diameter range with the associated guide segment 10, 102 to 105 is chosen. For this guide segment, the fitting or matching test system carrier 12, 106 to 109 is chosen. For connecting pipe seams, the saddle 8 and long test head holders 14, otherwise the outrigger unit 71, 110 and short test head holder 83 as well as the always compatible drive plate 50 must be held in readiness. The test manipulator 7 can then be assembled, as was explained with regard to FIGS. 1 to 7 and 8 to 14, respectively, at the testing site in one way or another, depending upon the local situation.

It is a great advantage of this construction that a test manipulator 7 can be put together at the site with only a few mutually compatible components relatively fast, which is adapted to a highly specialized test exercise, respectively. The assembly of the test manipulator is facilitated, in this regard, by the far-reaching use of fast-acting clamping fixtures 47 and 48 or clamping closures 51 and 52. Also, threading the respective race half-sections 45 and 46 into the associated guide segment can be facilitated yet further, in many cases, by constructing the guide segments in two parts, and by clamping the one side of each guide segment to the remaining part via bellcrank or toggle lever tighteners 111, 112 113 (FIG. 8). This also permits the guide segments to be slipped onto the race laterally. It is a further advantage that, with this manipulator, defined, exactly reproducible positioning of the test heads from a remote control console is possible. Ultrasonic oscillator heads, eddy current probes and detectors for gamma radiation are also thereby employable as test heads.

The foregoing is a description corresponding in substance to German Application No. P 33 29 483.6, dated Aug. 16, 1983, the International priority of which is being claimed for the instant application, and which is hereby made part of this application. Any material discrepancies between the foregoing specification and the aforementioned corresponding German application are to be resolved in favor of the latter.

We claim:

1. A test manipulator externally applicable to a pipe, adaptable for ultrasonically testing welded seams, the manipulator having a divided race for surrounding a pipe which is to be tested, a guide segment guided by the race at the periphery thereof, a test system carrier drivable in peripheral direction around a pipe, a driving and positioning device for the test system carrier and at least one test head holder fastenable to the test system carrier, comprising clamping means for fastening the race directly to the pipe in centered relationship to an adjustment mark located on the pipe; the guide segment mounted so as to be movable along the periphery of the race; an outrigger unit flangeable, together with the test system carrier and the test head holder, to said guide segment; and a saddle fastenable to the pipe in centered relationship to said adjustment mark; during testing of a pipe connection seam, said guide segment and the race, alternatively, being, respectively, movable on said saddle in axial direction of the pipe, and being, together with the test system carrier, rotatable on said guide segment in peripheral direction around the pipe.

2. A test manipulator according to claim 2, having a plurality of said races, said guide segments and said test system carriers of varying size for matching pipes to be tested which are of varying diameters, said driving and positioning device, said saddle and said outrigger unit being, in turn, matched in size thereto.

3. A test manipulator according to claim 2, including a plurality of said outrigger units, respectively, having strokes of varying length, said outrigger units being flangeable to all of said test system carriers.

4. A test manipulator according to claim 1, including fast-acting closures for connecting a plurality of the foregoing structural elements to one another.

5. A test manipulator according to claim 1, wherein said test head holder is movable parallel to the axis of the pipe on said outrigger unit fastened to said guide segment.

6. A test manipulator according to claim 5, wherein said outrigger unit carries a spindle extending parallel to the axis of the pipe, and a spindle unit mounted on said spindle for adjustably displacing said test head holder.

7. A test head manipulator according to claim 6 including a geared motor coupled to a pulse transmitter and operatively connected with said spindle unit for adjusting said unit.

8. A test manipulator according to claim 1, wherein said race is formed with a ring gear, and including a pinion carried by said guide segment and meshing with said ring gear for adjusting said guide segment relative to said race.

9. A test manipulator according to claim 8, including a geared motor and a pulse transmitter therefor clampable together on said guide segment, said pinion being drivable by said geared motor.

10. A test manipulator according to claim 1, wherein said adjusting mark is an adjustment pin carried by an adjustment ring clampable around the pipe to be tested.

11. A test manipulator according to claim 10, including cup springs for prestressing said adjustment ring to absorb thermal expansion.

12. A test manipulator according to claim 1, including an auxiliary bracket clampable on a pipe section and downwardly bent pipe elbow, respectively, for assembling the respective structural elements.

* * * * *